United States Patent [19]

Groger et al.

[11] Patent Number: 5,757,013
[45] Date of Patent: May 26, 1998

[54] FLUORESCENCE DECAY MEASUREMENT BY CALCULATION OF INNER PRODUCT

[75] Inventors: Howard P. Groger, Gainesville, Fla.; Russell J. Churchill, Radford, Va.; K. Peter Lo; Shufang Luo, both of Blacksburg, Va.

[73] Assignee: American Research Corporation of Virginia, Radford, Va.

[21] Appl. No.: 568,382

[22] Filed: Dec. 6, 1995

[51] Int. Cl.⁶ .......................................... F21V 9/16
[52] U.S. Cl. ............................ 250/458.1; 250/459.1; 356/317
[58] Field of Search .................. 250/458.1, 459.1, 250/461.1, 461.2; 356/317, 318, 417

[56] References Cited

U.S. PATENT DOCUMENTS

| | | |
|---|---|---|
| 4,594,511 | 6/1986 | Cooper et al. ............................. 250/351 |
| 5,030,832 | 7/1991 | Williams et al. ......................... 250/458.1 |
| 5,043,585 | 8/1991 | Fehrenback et al. .................... 250/458.1 |
| 5,063,297 | 11/1991 | Hardenbrook et al. ................. 250/458.1 |
| 5,196,709 | 3/1993 | Berndt et al. ............................ 250/458.1 |
| 5,212,386 | 5/1993 | Gratton et al. ........................... 250/458.1 |
| 5,270,548 | 12/1993 | Steinkamp ................................ 250/461.2 |
| 5,315,122 | 5/1994 | Pinsky et al. ............................. 250/461.2 |
| 5,317,162 | 5/1994 | Pinsky et al. ............................. 250/461.2 |
| 5,323,010 | 6/1994 | Gratton et al. ........................... 250/458.1 |
| 5,548,124 | 8/1996 | Takeshima et al. .................... 250/458.1 |

*Primary Examiner*—Don Wong
*Attorney, Agent, or Firm*—James Creighton Wray

[57] ABSTRACT

An apparatus and its accompanying method measures fluorescence decay, fluorescence amplitude and fluorescence polarization. The instrument includes a light emitting diode or laser diode light source, an amplified photodiode detector, and electronics and software for calculating the phase of the fluorescence from the computed inner product of the scattering and fluorescence signals. The electronics for measuring fluorescence decay includes two signal synthesizers, two downconverters, a simultaneously sampling analog-to-digital converter and means for calculating the inner product of the downconverted waveforms. A signal source, preferably a direct digital synthesizer, is used in combination with a digital-to-analog converter to provide a controllable output signal. That signal drives a modulatable light source, which is a light emitting diode, a laser diode or a combination of the two. Excitation light from the light source excites the sample fluorophore which is immobilized in a solid material. Fluorescence is detected using an amplified photodiode. The received signal is downconverted using a pair of mixers. The downconverted signals are digitized and stored. Preferably, the signals are digitized using a two-channel synchronous analog-to-digital converter controlled by a digital signal processor. Data from each channel are multiplied and summed to provide the inner product.

39 Claims, 4 Drawing Sheets

FLUORESCENCE DECAY MEASUREMENT BY CALCULATION OF INNER PRODUCT

BACKGROUND OF THE INVENTION

The present invention relates generally to fluorescence sensors for chemical detection and analysis.

Fluorescence decay is important in the field of chemical analysis. Unlike sensors which measure fluorescence amplitude, fluorescence decay instruments are less affected by changes in signal strength, stray light, scattering and changes in the geometry of the experimental set up. Instruments for measuring fluorescence decay are increasing in importance and have proven extremely effective in the calculation of dissolved oxygen levels in chemical and biological processes, in the measurement of chlorinated hydrocarbon concentration and in immunological assays. Unfortunately, existing fluorescence decay measurement instruments having the specificity, sensitivity and precision needed for effective analysis are extremely expensive. Needs exist for inexpensive apparatus and methods for monitoring fluorescence decay that meet the rigorous chemical analysis requirements presented in environmental, chemical process control, biological and biomedical applications.

Intensity-based detection of fluorescence requires reliable measurement of the intensity of the probe. In sub-surface applications fluorescence intensity is altered by changes in absorbance, by scattering, by optical misalignment and by the presence of multiple analytes. Needs exist for chemical sensing apparatus that detect phase rather than intensity, reduce system errors and allow for accurate measurement in the presence of interferents.

SUMMARY OF THE INVENTION

The present invention provides an inexpensive method for measuring fluorescence decay, fluorescence amplitude and fluorescence polarization in a single instrument using a light-emitting diode or laser diode light source, an amplified photodiode detector and electronics and software necessary to calculate the phase of the fluorescence through calculation of the inner product of the scattering and fluorescence signals.

An instrument for chemical detection measures fluorescence decay, fluorescence amplitude and fluorescence polarization. The phase of the fluorescence is determined using a modulatable source, a photodetector and electronics and software that calculate the inner product of the scattering and fluorescence signals.

For measuring fluorescence decay, the present invention includes a modulatable light source, a photodetector, signal synthesizers, downconverters, a simultaneously sampling analog-to-digital converter, and means for calculating the inner product of the downconverted waveforms. The instrument can be used with a light-emitting diode or a diode laser as a light source and the photodetector is an amplified photodiode. The instrument works with sinewave excitation and ranges of continuous functions approximating square and triangular waveforms.

An analog-to-digital converter provides near-simultaneous data acquisition from two channels. Dual channel synchronization provides phase accuracy. The present invention, unlike existing apparatus, acquires fluorescence decay data using a light emitting diode excitation source and an amplified photodiode detector. The light source is driven by a pair of direct digital synthesizers that generate a range of sinusoidal digital waveforms and deliver the waveforms to the light source through a digital-to-analog converter.

To provide a direct measure of phase delay caused by fluorescence decay, the present invention includes means for normalizing the excitation and fluorescence signals. Signal normalization is performed by measuring the maximum fluorescence and dividing the fluorescence at each sampling time by the fluorescence maximum. Another approach for signal normalization involves measuring the fluorescence with an amplifier/photodetector system having a large time constant that does not respond to the modulation signal. A digital signal processor provides signals for data acquisition. Data acquisition is started in the same portion of the excitation sine wave each cycle. For applications involving large sample numbers, the problem of starting point in the cycle is reduced.

When measuring the fluorescence decay in the frequency domain, the excitation source is modulated to provide a waveform given by $$E(t)=P_O(1+m_{ex}\sin 2\pi ft)$$

where $P_O$ is the direct current radiant power of the source and $m_{ex}$ is the ratio of the modulated component of the signal to the direct current component of the signal. The waveform of the fluorescence signal is given as $$F(t)=F'(1+m_f m_{ex}\sin(2\pi ft-\phi))$$

where F' is the dc component of the fluorescence signal, $m_f$ is the extent to which the fluorescence signal is demodulated and $\phi$ is the phase shift. The fluorescence lifetime is directly related to the phase shift through $\tau_p=\omega^{-1}\tan\phi$.

For a mixture of fluorophores, the fluorescence lifetime is determined through two independent measures, the relative phase and the relative modulation of the fluorescence emission for a range of modulation frequencies, $\omega$. Detection of the fluorescence lifetime is reduced to detection of phase differences between the excitation and the emission signals.

Preferably, the phase-modulation method of the present invention involves modulating the light source at frequencies ranging from 0.1 to 200 MHz. The phase shift or relative modulation is detected by standard radio-frequency techniques.

In the present invention, the phase of the fluorescence signal is measured through the inner product. The inner product for analog time sequences has been described according to the following equation:

$$<x(n),y(n)>=\int x(t)y(t)dt$$

where the integral extends over the time interval of interest. For discrete time sequences, the inner product is described as:

$$<x(n),y(n)>=\Sigma_n x(n)y(n)$$

where n is the sample number associated with the sampling time, t. The inner product is a measure of similarity of two continuous time waveforms. The advantages in using the inner product rather than cross-correlation include:

The inner product is less computationally intensive than digital cross-correlation methods.

The inner product can be performed using a low-cost instrument and is compatible with extremely low-cost instrumentation.

The increase in data samples usable in a low-cost instrument provides an advantage in accuracy at a small number of frequencies.

The benefits of computing the inner product with increased numbers of samples is found in the argument for signal averaging. For the output signal r(t) containing the fluorescence waveform s(t) plus noise n(t), averaging the signal provides $$s_{avg}(t) = 1/N \; \Sigma r(t_i) = s(t) + 1/N \; \Sigma n(t_i)$$

If the RMS noise level in any single measurement window is $\sigma$, the standard error SE of a series of N measurements is $\sigma/\sqrt{N}$. That is because the net noise power $(SE)^2$ is given in terms of the expected value as $$(SE)^2 = 1/N^2 \Sigma\Sigma E(n(t_i)n(t_j)) = 1/N^2 \Sigma E(n^2(t_i)) = N \; 1/N^2 \sigma^2 \text{ or } \sigma^2/N$$

Existing methods and apparatus fluorescence decay detection has proven inadequate. Those methods and apparatus accomplish phase detection in fluorescence decay using cross-correlation, phase locked loops and pulse methods. The present invention eliminates the limitations and inefficiencies that afflict existing fluorescence decay based sensors. Advantages recognized by the present invention include:

- The present invention is applicable to long lifetime fluorophores such as metal-ligand complexes and materials useful for temperature measurement.
- The inner product calculation of the present invention is well suited for calculation of phase in a low-cost instrument.
- The present invention has specific methods for computing the phase.
- The present invention uses a novel photodiode/light emitting diode configuration.
- Calculation of the inner product allows long-time signal acquisition and results in increased sensitivity when used with stable fluorophores.
- The digital signal processor incorporated in the present invention provides fluorescence amplitude data for signal normalization. In some cases, it is usable as one or more independent means of signal characterization.

The present invention has numerous potential applications in the area of chemical detection. Low-cost sensors based on integrated circuit versions of the present invention and eddy current instrumentation using the present invention are attractive options to all companies involved in chemical detection apparatus.

These and further and other objects and features of the invention are apparent in the disclosure, which includes the above and ongoing written specification, with the claims and the drawings.

DETAILED DESCRIPTION OF THE PREFERRED EMBODIMENTS

Figure 1:
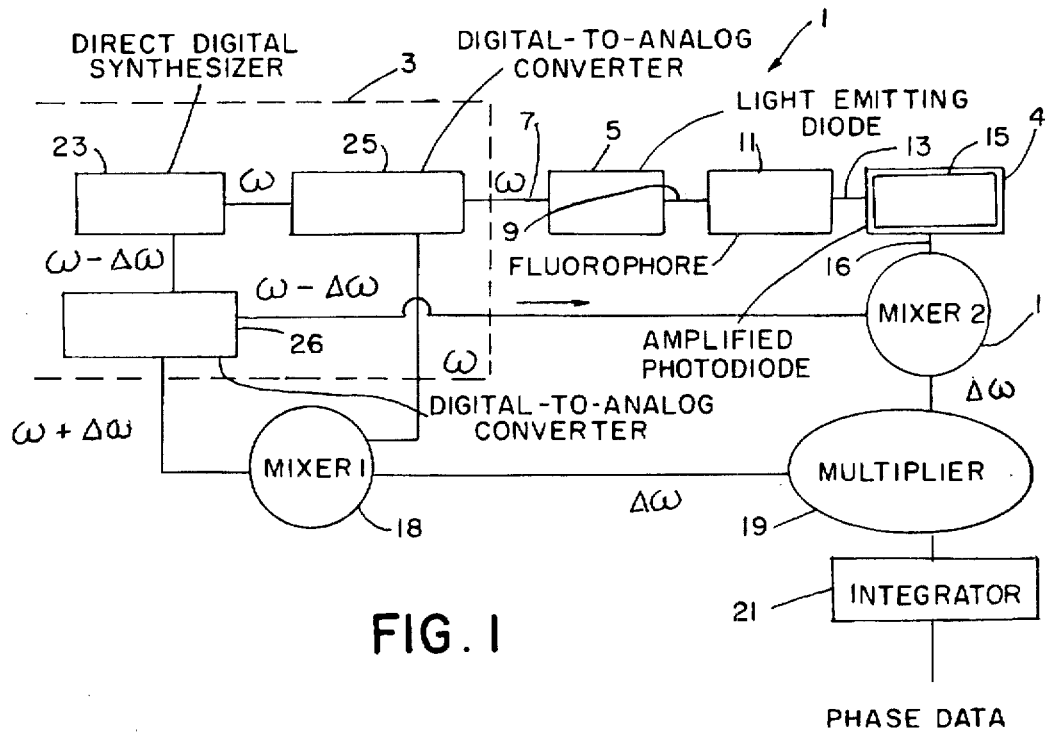
FIG. 1 is a schematic illustration of the fluorescence sensor of the present invention.

Referring to FIG. 1, the sensor apparatus 1 for measuring fluorescence decay includes a signal generator 3 and a modulatable light source 5. The light source 5 is driven by analog signals 7 generated by the signal generator 3. Light signals 9 are directed from the light source 5 onto a fluorophore 11. Fluorescence signals 13 from the excited fluorophore 11 are detected by a photodetector 15. The received signals 16 are demodulated by a mixer 17. A multiplier 19 receives demodulated fluorescence signals from the mixer 17 and reference signals and generates fluorescence and reference waveforms. The reference signals are preferably derived from one or more channels including a polarization beamsplitter in series with the fluorophore 11 but prior to the photodetector 15. The waveforms are delivered to an integrator 21, which computes an inner product from the fluorescence and reference waveforms. The inner product is calculated at a single frequency and wavelength or at multiple frequencies and wavelengths.

The signal generator 3 can be a direct digital synthesizer 23, an oscillator, a voltage controlled oscillator or a phase-locked loop. In preferred embodiments, the signal generator 3 is a low cost direct digital synthesizer 23 having a phase accuracy in excess of 0.001 degrees and capable of providing quadrature signals for phase determination.

As shown in FIG. 1, a preferred embodiment of the sensor 1 includes a direct digital synthesizer 23 used with digital-to-analog converters 25, 26 to provide a controllable output signal 7 in a range of frequencies up to 25 MHz. The signal 7 from the digital-to-analog converters drives the light source 5. The signals 7 from the digital-to-analog converters 25 may be filtered in a filter bank that includes filters selected to correspond to a frequency of interest.

The light source 5 is preferably a modulatable light source having one or more stages of modulation. Preferably, the light source 5 includes at least one light emitting diode or laser diode. In one embodiment, the light source 5 is a combination of at least one light emitting diode and at least one laser diode. For applications involving the concentration measurement of dissolved oxygen, the sensor preferably has a light emitting diode having a peak output of 450 nm as the light source 5.

More than one light source can be used to excite the fluorophore. In a preferred embodiment blue, green, yellow, red and/or infrared light emitting diodes are alternatively used to provide data on fluorescence decay at more than one wavelength. Similarly, multiple diode lasers having wavelengths selected for a particular fluorophore of interest can be used. Preferably, the light emitting diodes or laser diodes have output powers of 0.5 mW or higher. Alternatively, multiple fluorophores are used to provide simultaneous data.

Fluorescence 13 from the excited fluorophore 11 is detected with considerable gain. Preferably the circuits included in the sensor are produced using radiofrequency design methods to meet the requirements imposed by the considerable gain.

Figure 2:
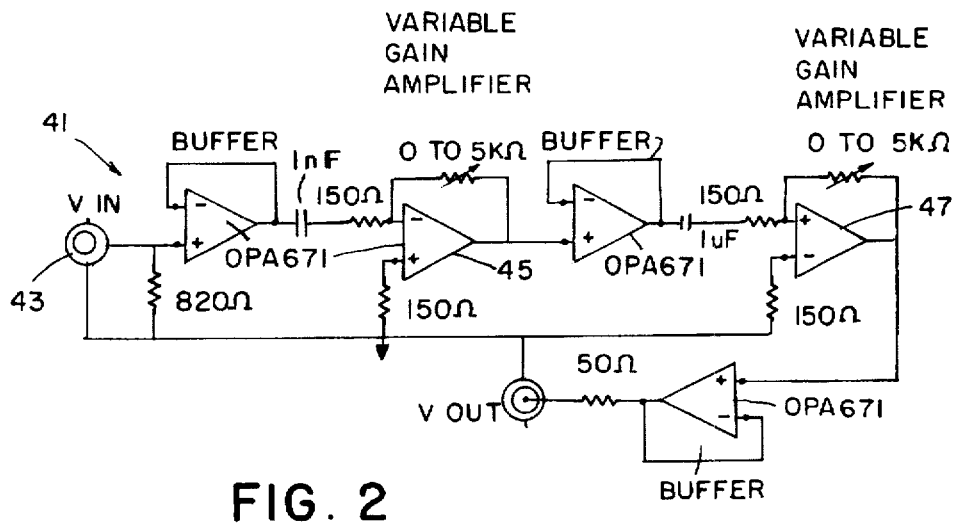
FIG. 2 shows a preferred amplifier circuit diagram for use in the present invention.

The fluorescence signals are detected by at least one photodetector 15. A shield 4 may be provided around the photodiode 15. Numerous photodetectors are compatible with for use with the present invention, including but not limited to an intensified charge couple device, a photomultiplier tube, an avalanche photodiode and an amplified photodiode. For applications requiring amplifications in the 1,000,000 to 1,000,000,000 range, a set of amplifiers as well as the localized amplifier is used. FIG. 2 shows a preferred amplifier circuit diagram for use in the present invention. In that application 41, the photodiode is preferably powered by an isolated power supply 43, shielded from digital equipment including any direct digital synthesizers, and positioned a short distance from the amplifiers 45, 47 to reduce interference.

In a preferred embodiment the photodetector 15 is an array of photodiodes having nonlinear amplifier elements. In that embodiment, demodulation is performed for each element, and the resulting array of inner products provides an image for two-dimensional fluorescence decay monitoring.

Figure 3:
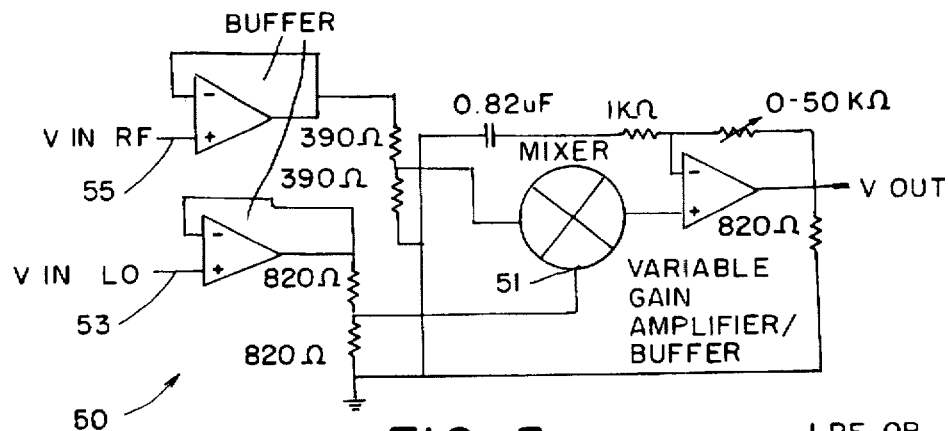
FIGS. 3 and 4 show two possible mixer circuits for downconverting the detected signals.
Figure 4:
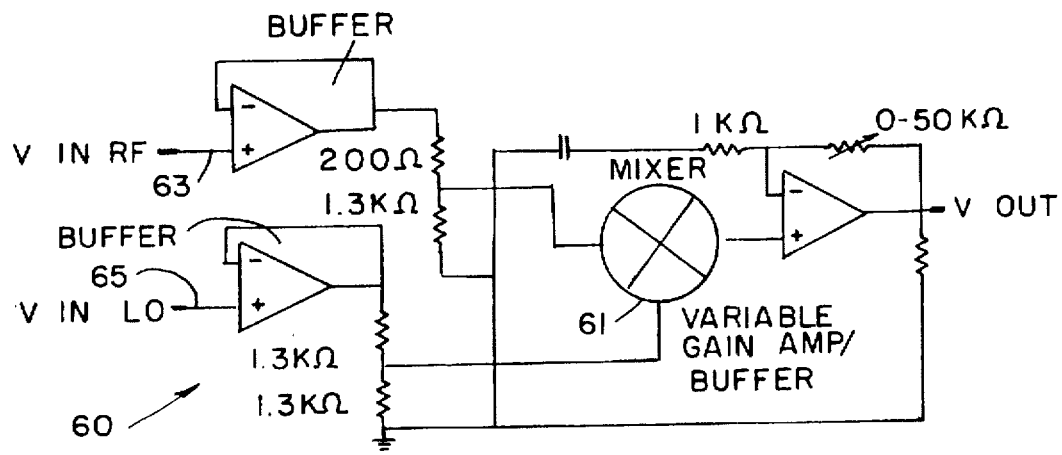

The detected signal 16 is delivered from the photodetector 15 to a demodulator, such as a downconverter. Preferably the downconverter includes a pair of mixer circuits 17, 18. FIGS. 3 and 4 show two possible mixer circuits 50 and 60 for downconverting the detected signals. In one embodiment, a first radio-frequency mixer 51 mixes signals 53 from a fluorescence channel with signals 55 generated at frequency different from the frequency of modulation. A second radio-frequency mixer 61 separately mixes signals 63 from a reference channel with the signals 65 generated at frequency different from the frequency of modulation. In that embodiment, the fluorescence channel includes a photodetector 15 positioned in the vicinity of the excited fluorophore 11 and an interference coating or light filter positioned over the photodetector 15 for preventing scattered light from entering the channel. The reference channel does not include an interference coating or filter for filtering scattered light. Preferably, two separate signal and reference channels are used, with one channel for the region of fluorophore exposed to the analyte and a second channel for the region of the fluorophore not exposed to the analyte.

In one embodiment of the present invention, the demodulation of the signals are performed by analog multiplication and low pass filtering.

In another embodiment of the present invention, demodulation of the signals includes rapid digital data acquisition followed by digital data manipulation. Digital data manipulation includes digital signal multiplication and digital decimation filtering.

The demodulated signals are digitized and stored. In embodiments of the present invention, digitization is performed using a two-channel synchronous analog-to-digital converter controlled by a digital signal processor. Data from the fluorescence and reference channels of the analog-to-digital converter at a sample interval are multiplied and summed to provide an inner product. A variable analog delay line can be used to accomplish the same results. The average maximum and minimum of the sinusoidal fluorescence and reference waveforms are determined for 1024 points and subtracted from the signal array set to remove the DC offset of each signal and reference point. The DC offset is computed as the average maximum minus the average minimum divided by two and added to the average minimum. When direct digital synthesizers in combination with digital-to-analog converters are used as the signal generator, a controller regulates the phase offset registers of a first direct digital synthesizers and alters the frequency of a second direct digital synthesizer to provide a known downconversion frequency.

In a preferred embodiment of the sensor, the demodulated signals are digitized using a dual sampling analog-to-digital converter. Phase information is preserved as a single synchronization pulse triggers a near simultaneous acquisition of data from both the fluorescence channel and the reference channel.

The downconverted signals may be digitized at a rate substantially between 20 MegaSamples per second and 500 MegaSamples per second using low-cost, high-speed analog-to-digital converters. Signals from the low-cost, high-speed analog-to-digital converters are input to a set of digital downconverters to provide digital signals at frequencies usable for computing an inner product. The digital downconverters used in the low-cost, high-speed analog-to-digital converters preferably include a complex sinusoid generator, a high decimation filter and a low pass finite impulse response filter for providing in-phase and quadrature components of the signal and the reference waveforms.

The phase difference between the fluorescence channel and the reference channel is determined from the inner product by calculating the maximum and minimum points of the waveform, removing the signal bias and normalizing the digitized data. The normalized data is compared to a look-up table. The look-up table is calculated by piecewise multiplying two normalized waveforms having known phase lags between the waveforms and then summing over the same number of samples as taken in the measurement. In an alternative embodiment, the data of the inner products of two phase shifted waveforms are calculated and a high-order polynomial is fit to the data to allow determination of phase delay. That determination is accomplished by substituting the normalized inner product in the polynomial expression of the inner product.

The difference between the calculated maxima and minima of the signal waveform provides data on signal modulation.

In a preferred embodiment, signal amplitude is calculated by acquiring the waveform of the downconverted signal, forming the Fourier transform of the downconverted signal and determining the amplitude of the transformed signal in frequency domain at the difference frequency.

Preferably, phase data is acquired using a fast analog-to-digital converter and amplitude data is acquired using a slower analog-to-digital converter.

Fluorescence amplitude is determined by the present sensor by digitally integrating the signal from the fluorescence channel or by digitally averaging maxima and minima for each cycle.

Light from the light source excites a fluorophore. In one embodiment of the present invention the fluorophore is immobilized in a solid material. Possible materials for holding the fluorophore include polymers, gels and ceramic materials. In another embodiment of the present invention, the sensor includes a sample compartment into which the fluorophore is introduced. The fluorophore remains in the compartment for a time sufficient for calculating the fluorescence decay.

Preferably, the waveforms approximate logic pulse and a pulse-to-digital converter is used to provide digital processing of the resulting data.

Figure 5:
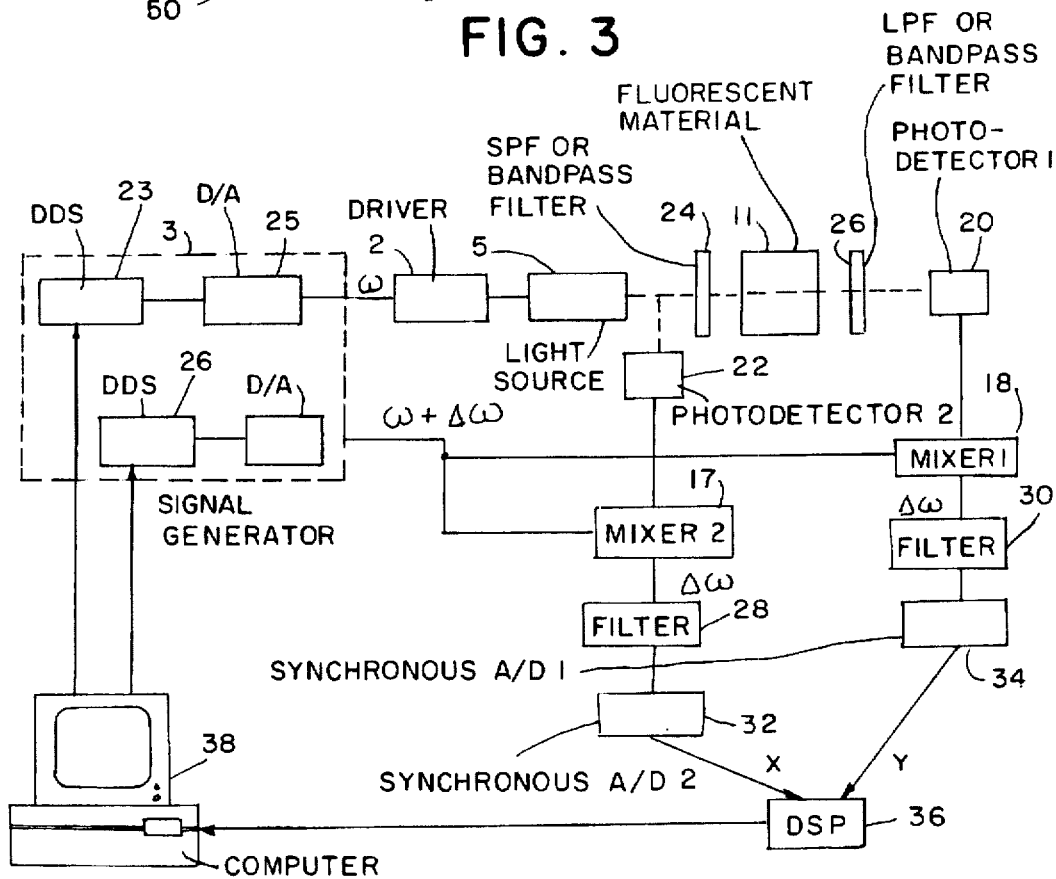
FIG. 5 shows a fluorescence decay system circuit diagram.

FIG. 5 shows a schematic of a fluorescence decay system. FIG. 5 shows the sensor apparatus for measuring fluorescence decay of a fluorophore 11 having a signal generator 3, having a digital synthesizer or a phase-lock loop 23 and a digital-to-analog converter 25, for generating signals, a modulatable light source 5 (either a laser diode or a light-emitting diode or a combination of the two) that is connected to a driver 2 and is driven by signals generated by the signals generator, a photodetector 20 for detecting fluorescence signals, a fluorophore 11 positioned between the light source and the photodetector for receiving light from the light source and for delivering fluorescence signals to the photodetector, a digitizer for digitizing the fluorescence signals and reference signals and for generating fluorescence and reference waveforms, and a computer 38 and/or a digital-signal processor 36 for computing an inner product from the fluorescence and reference waveforms, for determining and outputting a phase difference between the fluorescence and reference waveforms. Additionally, mixers 17, 18, filters 28, 30, and analog-to-digital converters 32, 34 may be provided between the photodetectors 20, 22 and the digital signal processor 36.

Figure 6:
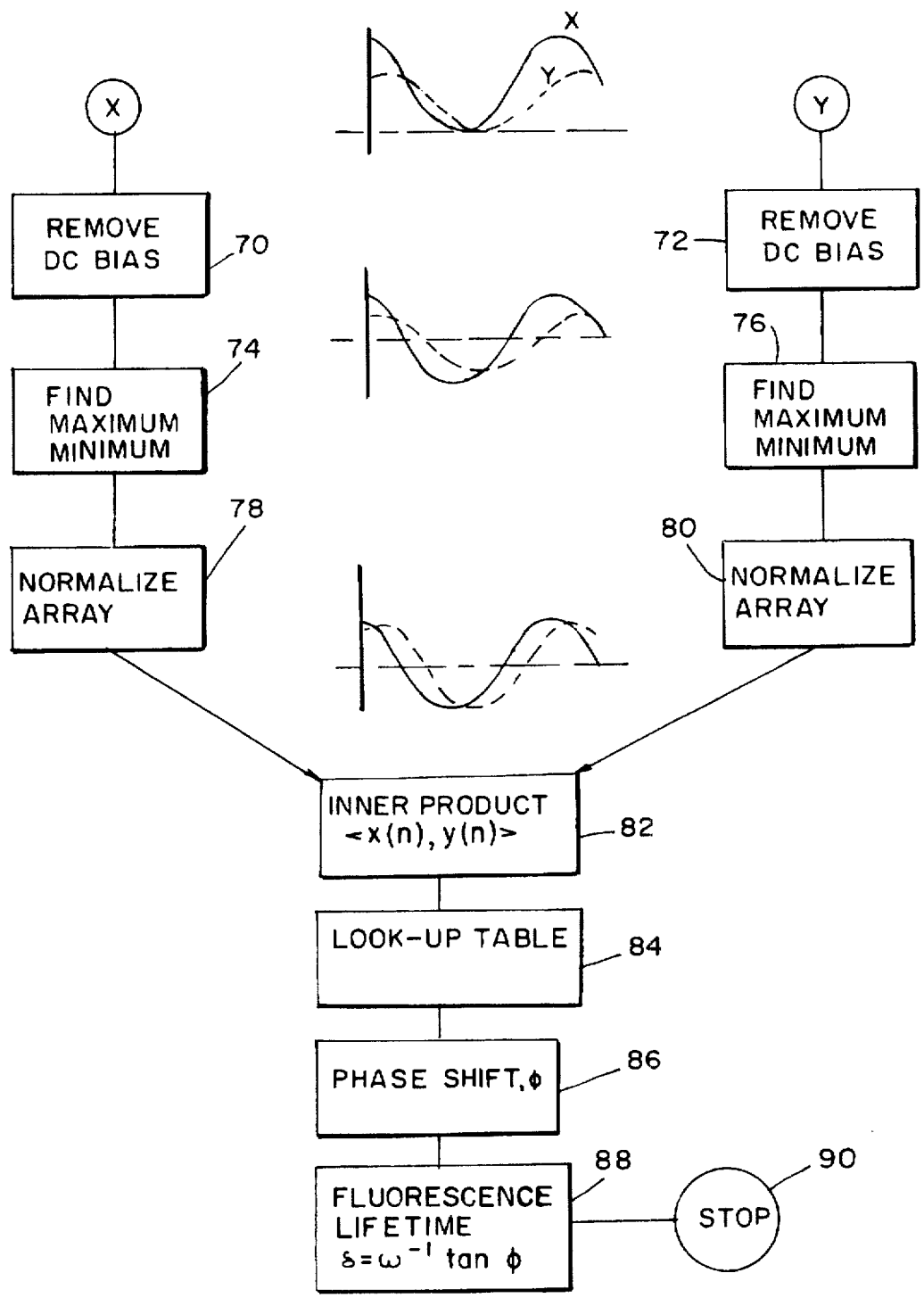
FIG. 6 is a flow chart for computing phase shift.

FIG. 6 shows the method of computing phase shift. The method includes generating a reference signal, delivering the reference signal to a light source, directing light from the light source to a region containing a fluorophore, detecting fluorescence emitted by the fluorophore with a photodetector, generating fluorescence signals, demodulating the fluorescence signals and reference signal and creating demodulated signals, obtaining waveforms from the digitized signals by the steps shown in 70, 72, 74, 76, 78 and 80, and calculating an inner product 82 from the waveforms and determining 84 and outputting 90 a phase difference 86 between the fluorescence signals 88 and the reference signal.

Figure 7:
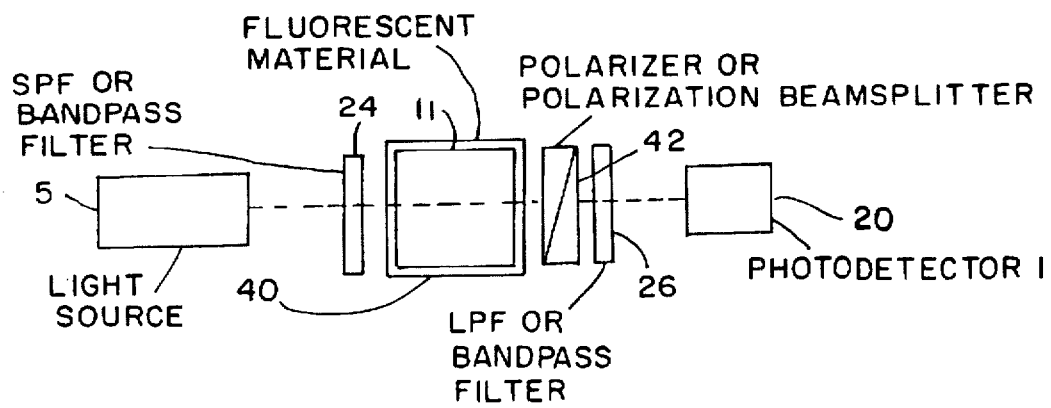
FIG. 7 is a schematic illustration of a polarization beamsplitter.

FIG. 7 shows a polarization beamsplitter 42 between the light source 5 and the photodetector 20 along with the LPF (low pass filter) or bandpass filter 24, 26. A compartment 40 may be provided for the fluorophore 11.

For applications involving the concentration measurement of dissolved oxygen, the sensor preferably has a light emitting diode having a peak output of 450 nm as the light source. The sensor is used at the 50 kHz to 150 kHz range, which allows for the use of an amplified photodiode photodetector, such as the OPT 211 amplified photodiode from Burr Brown. When higher frequencies are used, the photodetector includes other amplified photodiodes such as the SD-041-41-44-211 from Advanced Photonics.

The sensor of the present invention has potential uses for eddy current measurement. The eddy current sensor measures and compares voltage and current waveforms, uses windings of an eddy current probe in place of a light source, and does not require a fluorophore or photodetector. The sensor includes a signal generator, an eddy current probe that is driven by signals generated by the signal generator, coils surrounding the eddy current probe, a demodulator for demodulating eddy current signals, a digitizer for digitizing the demodulated signals by the signal generator and for generating voltage and current waveforms, and a comparator for computing an inner product from the current and voltage waveforms.

While the invention has been described with reference to specific embodiments, modifications and variations of the invention may be constructed without departing from the scope of the invention, which is defined in the following claims.

We claim:

1. A sensor apparatus for measuring fluorescence decay of a fluorophore comprising a source for generating reference signals, a signal generator for generating signals, a modulatable light source that is driven by signals generated by the signals generator, a photodetector for detecting fluorescence signals, a fluorophore positioned between the light source and the photodetector for receiving light from the light source and for delivering fluorescence signals to the photodetector, a demodulator for demodulating the fluorescence signals, a digitizer for digitizing the demodulated fluorescence signals and reference signals and for generating fluorescence and reference waveforms, and a computer or a digital-signal processor for computing an inner product from the fluorescence and reference waveforms, for determining and outputting a phase difference between the fluorescence and reference waveforms.

2. The apparatus of claim 1, wherein the demodulator is first and second mixers, the first mixer positioned for receiving the fluorescence signals from the photodetector, and the second mixer positioned for receiving reference signals from the signal generator, and wherein the signals in the first mixer and the signals in the second mixer are each mixed with a different frequency signal generated at a frequency different from a modulation frequency.

3. The apparatus of claim 2, wherein the photodiode in the first mixer has a coating for preventing scattered light from entering the mixer.

4. The apparatus of claim 1, further comprising providing the fluorophore in a solid material for immobilizing the fluorophore.

5. The apparatus of claim 4, wherein the solid material is selected from the group consisting of a polymer, a gel and a ceramic material.

6. The apparatus of claim 1, further comprising a compartment positioned between the light source and the photodetector for carrying the fluorophore.

7. The apparatus of claim 1, wherein the signal generator is selected from a group consisting of an oscillator, a digital synthesizer and a phase-lock loop.

8. The apparatus of claim 1, wherein the signal generator is at least one direct digital synthesizer having phase accuracy in excess of 0.001 degrees.

9. The apparatus of claim 8, further comprising at least one digital-to-analog converter positioned between the at least one synthesizer and the light source for receiving signals from the at least one synthesizer and for delivering a controllable output signal to the light source for driving the light source.

10. The apparatus of claim 1, wherein the modulatable light source is selected from the group consisting of a light emitting source, a laser diode, and a combination of at least one light emitting source and at least one laser diode.

11. The apparatus of claim 1, further comprising an analog-to-digital converter and a digital signal processor for controlling the analog-to-digital converter.

12. The apparatus of claim 11, wherein the analog-to-digital converter is a two channel synchronous analog-to-digital converter.

13. The apparatus of claim 11, wherein the analog-to-digital converter is a dual sampling analog-to-digital converter such that a single synchronization pulse triggers an acquisition of data from both fluorescence and reference channels in a near simultaneous manner.

14. The apparatus of claim 1, further further comprising an analog multiplier for multiplying signals from the photodetector and a low pass filter for filtering the multiplied signals.

15. The apparatus of claim 1, further comprising a non-linear circuit element and a low pass filter.

16. The apparatus of claim 1, wherein the demodulator comprises a digital downconverter.

17. The apparatus of claim 16, further comprising a digital signal multiplier and a digital decimation filter.

18. The apparatus of claim 1, wherein the signal generator is a first direct digital synthesizer and a digital-to-analog converter, and wherein the demodulator is a second direct digital synthesizer.

19. The apparatus of claim 1, further comprising a polarization beamsplitter positioned in series with the fluorophore and between the fluorophore and the photodetector.

20. The apparatus of claim 1, wherein the photodetector is selected from a group consisting of a charge coupled device, a photomultiplier tube, an avalanche photodiode and an amplified photodiode.

21. The apparatus of claim 1, wherein the photodetector is an amplified photodiode having amplification in a 1,000, 000 to 1,000,000,000 range.

22. The apparatus of claim 21, wherein the amplified photodiode comprises multiple amplifiers, a photodiode and an power supply.

23. The apparatus of claim 22, further comprising a shield positioned around the amplified photodiode.

24. The apparatus of claim 22, wherein the amplifiers are positioned spaced from the photodiode to reduce interference.

25. The apparatus of claim 1, wherein the light source is multiple light emitting diodes, the diodes emitting light selected from the group consisting of blue light, green light, yellow light, red light and infrared light.

26. The apparatus of claim 1, wherein the light source has an output power of at least 0.5 milliwatts.

27. The apparatus of claim 1, wherein the signal generator comprises a direct digital synthesizer, a digital-to-analog converter.

28. The apparatus of claim 1, wherein the digitizer comprises a first analog-to-digital converter for obtaining phase data and a second analog-to-digital converter for obtaining amplitude data.

29. A method for chemical detection comprising generating a reference signal, delivering the reference signal to a light source, directing light from the light source to a region containing a fluorophore, detecting fluorescence emitted by the fluorophore with a photodetector, generating fluorescence signals, demodulating the fluorescence signals and reference signal and creating demodulated signals, obtaining waveforms from the digitized signals and calculating an inner product from the waveforms and determining and outputting a phase difference between the fluorescence signals and the reference signal.

30. The method of claim 29, wherein the demodulating step comprises downconverting the reference and fluorescence signals.

31. The method of claim 29, wherein the demodulating step further comprises mixing the fluorescence signals with a signal generated at a frequency different from a frequency of modulation, and mixing the reference signal separately with the signal generated at a frequency different from a frequency of modulation.

32. The method of claim 31, further comprising providing the photodetector with a coating to prevent substantial quantities of scattered light from entering the photodetector.

33. The method of claim 29, wherein generating the reference signal comprises synthesizing a digital signal and converting the digital signal to an analog reference signal.

34. The method of claim 29, wherein the calculating step comprises piecewise multiplying the demodulated signal and the reference signal and computing a running sum.

35. The method of claim 29, further comprising calculating a phase difference between the reference and the fluorescence signals from the inner product, the calculating of phase difference further comprising determining maximum and minimum points of the waveforms, removing signal bias, normalizing resulting data with respect to amplitude, comparing the data with a look-up table and summing over a number of samples as taken in the measurement.

36. The method of claim 29, wherein the demodulating step further comprises multiplying the signals and low-pass filtering the multiplied signals.

37. The method of claim 29, wherein the demodulating step further comprises mixing the signals and low-pass filtering the mixed signals.

38. The method of claim 29, further comprising determining fluorescence amplitude, the determining step selected from a group consisting of digitally integrating fluorescence signals and digitally averaging maximum and minimum fluorescence signals for a predetermined cycle.

39. The method of claim 38, wherein determining fluorescence amplitude further comprises downconverting a fluorescence signal, acquiring a waveform of the downconverted signal, forming a Fourier transform of the downconverted signal and obtaining an amplitude of the transformed signal in a frequency domain at a different frequency.

* * * * *